United States Patent
Madden et al.

(10) Patent No.: US 10,776,654 B2
(45) Date of Patent: Sep. 15, 2020

(54) ASSESSMENT OF LIPID CORE PLAQUE INTEGRITY

(71) Applicant: InfraReDx, Inc., Burlington, MA (US)

(72) Inventors: Sean P. Madden, Arlington, MA (US); Joel S. Raichlen, Bryn Mawr, PA (US)

(73) Assignee: InfraReDx, Inc., Burlington, MA (US)

( * ) Notice: Subject to any disclaimer, the term of this patent is extended or adjusted under 35 U.S.C. 154(b) by 969 days.

(21) Appl. No.: 15/061,730

(22) Filed: Mar. 4, 2016

(65) Prior Publication Data
US 2016/0267360 A1    Sep. 15, 2016

Related U.S. Application Data

(60) Provisional application No. 62/131,140, filed on Mar. 10, 2015.

(51) Int. Cl.
*A61B 5/02*    (2006.01)
*A61B 5/00*    (2006.01)
(Continued)

(52) U.S. Cl.
CPC .......... *G06K 9/4652* (2013.01); *A61B 1/3137* (2013.01); *A61B 5/0075* (2013.01); *A61B 5/0086* (2013.01); *A61B 5/02007* (2013.01); *A61B 5/7264* (2013.01); *G06T 7/0012* (2013.01); *G06T 7/12* (2017.01);
(Continued)

(58) Field of Classification Search
CPC ... A61B 5/0075; A61B 5/0086; A61B 5/0084; A61B 1/043; A61B 1/07
See application file for complete search history.

(56) References Cited

U.S. PATENT DOCUMENTS

| 5,441,053 A | 8/1995 | Lodder et al. |
| 6,475,159 B1 | 11/2002 | Casscells et al. |

(Continued)

FOREIGN PATENT DOCUMENTS

| JP | 2005534428 A1 | 11/2005 |
| JP | 2007531598 A1 | 11/2007 |

(Continued)

OTHER PUBLICATIONS

510(K) Summary: LipiScan Coronary Imaging System, K072932, submitted by InfraReDx, Inc., 2008, available at http://www.accessdata.fda.gov/cdrh_docs/pdf7/K072932.pdf.

(Continued)

*Primary Examiner* — Baisakhi Roy
(74) *Attorney, Agent, or Firm* — Proskauer Rose LLP

(57) ABSTRACT

Methods, devices and systems, including computer-implemented methods for building a lipid core plaque (LCP) cap collagen structural integrity classifier are described. The blood vessel wall is illuminated with near-infrared light. Reflected near-infrared light from the blood vessel wall is received. A reflectance spectrum based on the reflected near-infrared light from the blood vessel wall is determined. Whether the reflectance spectrum is indicative of the presence of an LCP is determined. Collagen structural integrity indicator data associated with the blood vessel wall are determined. The LCP cap collagen structural integrity classifier is generated based on the reflectance spectrum and the collagen structural integrity indicator data.

10 Claims, 8 Drawing Sheets

(51) Int. Cl.
| | |
|---|---|
| *G06K 9/62* | (2006.01) |
| *G06K 9/46* | (2006.01) |
| *G06K 9/20* | (2006.01) |
| *G06T 7/12* | (2017.01) |
| *A61B 1/313* | (2006.01) |
| *G06T 7/00* | (2017.01) |
| *A61M 5/00* | (2006.01) |

(52) U.S. Cl.
CPC .... *A61M 5/007* (2013.01); *G06T 2207/10024* (2013.01); *G06T 2207/20168* (2013.01); *G06T 2207/30024* (2013.01); *G06T 2207/30101* (2013.01)

(56) References Cited

U.S. PATENT DOCUMENTS

| | | |
|---|---|---|
| 6,615,062 B2 | 9/2003 | Ryan et al. |
| 6,654,630 B2 | 11/2003 | Zuluaga et al. |
| 6,701,181 B2 | 3/2004 | Tang et al. |
| 6,706,004 B2 | 3/2004 | Tearney et al. |
| 6,816,743 B2 | 11/2004 | Moreno et al. |
| 6,873,868 B2 | 3/2005 | Furnish |
| 6,895,137 B2 | 5/2005 | Zuluaga et al. |
| 6,904,199 B2 | 6/2005 | Zuluaga |
| 6,949,072 B2 | 9/2005 | Furnish et al. |
| 6,980,573 B2 | 12/2005 | Korn |
| 7,132,645 B2 | 11/2006 | Korn |
| 7,190,464 B2 | 3/2007 | Alphonse |
| 7,292,715 B2 | 11/2007 | Furnish |
| 7,310,357 B2 | 12/2007 | Zuluaga et al. |
| 7,313,432 B2 | 12/2007 | Tearney |
| 7,340,083 B2 | 3/2008 | Yuan et al. |
| 7,376,456 B2 | 5/2008 | Marshik-Geurts et al. |
| 7,426,410 B2 | 9/2008 | Zuluaga et al. |
| 7,450,241 B2 | 11/2008 | Zuluaga |
| 7,486,985 B2 | 2/2009 | Marshik-Geurts et al. |
| 7,535,935 B2 | 5/2009 | Korn |
| 7,539,530 B2 | 5/2009 | Caplan et al. |
| 7,603,166 B2 | 10/2009 | Casscells, III et al. |
| 7,616,321 B2 | 11/2009 | Korn |
| 7,672,713 B2 | 3/2010 | Furnish |
| 7,679,754 B2 | 3/2010 | Zuluaga |
| 7,689,268 B2 | 3/2010 | Marshik-Geurts et al. |
| 7,742,805 B2 | 6/2010 | Furnish et al. |
| 7,873,406 B2 | 1/2011 | Furnish et al. |
| 7,889,348 B2 * | 2/2011 | Tearney ............... A61B 1/043 356/451 |
| 7,929,145 B2 | 4/2011 | Zuluaga |
| 8,000,774 B2 | 8/2011 | Sum et al. |
| 8,060,187 B2 | 11/2011 | Marshik-Geurts et al. |
| 8,774,905 B2 * | 7/2014 | Waxman ............ A61B 5/02007 600/475 |
| 2001/0047137 A1 * | 11/2001 | Moreno ............... A61B 5/0075 600/475 |
| 2002/0045811 A1 | 4/2002 | Kittrell et al. |
| 2004/0077950 A1 * | 4/2004 | Marshik-Geurts ... A61B 5/0075 600/475 |
| 2004/0266734 A1 | 12/2004 | Danenberg et al. |
| 2006/0058592 A1 | 3/2006 | Bouma et al. |
| 2007/0167836 A1 | 7/2007 | Scepanovic et al. |
| 2008/0015448 A1 * | 1/2008 | Keely ................. A61B 5/0091 600/477 |
| 2008/0249751 A1 | 10/2008 | Gadkar et al. |
| 2009/0317856 A1 * | 12/2009 | Mycek ................ A61B 5/0071 435/29 |
| 2010/0317974 A1 | 12/2010 | Alfano et al. |
| 2010/0330611 A1 * | 12/2010 | Mycek ................ A61B 5/0071 435/29 |
| 2011/0306956 A1 | 12/2011 | Islam |
| 2012/0101391 A1 | 4/2012 | Okada et al. |
| 2012/0129818 A1 | 5/2012 | Rajagopal |
| 2012/0245473 A1 * | 9/2012 | Mycek ................ A61B 5/0071 600/479 |
| 2012/0302892 A1 | 11/2012 | Lue et al. |
| 2013/0053698 A1 * | 2/2013 | Madden ............... A61B 5/0075 600/473 |
| 2015/0150461 A1 | 6/2015 | Madden et al. |

FOREIGN PATENT DOCUMENTS

| | | |
|---|---|---|
| JP | 2008510585 A1 | 4/2008 |
| JP | 2009254794 A1 | 11/2009 |
| WO | 2004012586 A2 | 12/2004 |
| WO | 2005096921 A1 | 10/2005 |
| WO | 2010131697 A1 | 11/2010 |

OTHER PUBLICATIONS

510(K) Summary: InfraReDx LipiScan™ IVUS Imaging System, K093993, submitted by InfraReDx, Inc., 2010, available at http://www.accessdata.fda.gov/cdrh_docs/pdf9/K093993.pdf.

R. Virmani et al., "Pathology of the Vulnerable Plaque", J. Am. Coll. Cardiol. 2006; 47:C13-18.

E. Falk et al., "Coronary Plaque Disruption", Circulation 1995; 92:657-671, available at http://circ.ahajournals.org/content/92/3/657.short.

A. Finn et al., "Concept of Vulnerable/Unstable Plaque", Journal of the American Heart Association, Arteriosclerosis, Thrombosis, and Vascular Biology 2010; 30:1282-1292, available at http://atvb.ahajournals.org/content/30/7/1282.

G. Stone et al., "A Prospective Natural-History Study of Coronary Atherosclerosis", The New England Journal of Medicine 2011; 364:226-235.

H. Garcia-Garcia et al., "Tissue characterisation using intravascular radiofrequency data analysis: recommendations for acquisition, analysis, interpretation and reporting", EuroIntervention 2009; 5:177-189.

S. Takarada et al., "Effect of statin therapy on coronary fibrous-cap thickness in patients with acute coronary syndrome: Assessment by optical coherence tomography study", Atherosclerosis 2009; 202:491-497, available at www.elsevier.com/locate/atherosclerosis.

S. Chia et al., "Association of statin therapy with reduced coronary plaque rupture: an optical coherence tomography study", NIH Public Access Coron. Artery. Dis. Author Manuscript, published in final edited form as: Coron. Artery Dis. Jun. 2008; 19(4): 237-242.

G. van Soest et al., "Pitfalls in Plaque Characterization by OCT: Image Artifacts in Native Coronary Arteries", J. Am. Coll. Cardiol. Img. 2011; 4;810-813, available at http://imaging.onlinejacc.org/cgi/content/full/4/7/810.

W. Jaross et al., "Determination of cholesterol in atherosclerotic plaques using near infrared diffuse reflection spectroscopy", Atherosclerosis 1999; 147:327-337.

V. Neumeister et al., "Determination of the cholesterol-collagen ratio of arterial atherosclerotic plaques using near infrared spectroscopy as a possible measure of plaque stability", Atherosclerosis 2002; 165:251-257.

C. Gardner et al., "Detection of Lipid Core Coronary Plaques in Autopsy Specimens With a Novel Catheter-Based Near-Infrared Spectroscopy System", J. Am. Coll. Cardiol. Img. 2008; 1:638-648, available at http://imaging.onlinejacc.org/cgi/content/full/1/5/638.

L. Rokach, "Taxonomy for characterizing ensemble methods in classification tasks: A review and annotated bibliography", Computational Statistics & Data Analysis 2009; 53:4046-4072.

P. Moreno et al., "Detection of Lipid Pool, Thin Fibrous Cap, and Inflammatory Cells in Human Aortic Atherosclerotic Plaques by Near-Infrared Spectroscopy", Circulation 2002; 105:923-927, available at http://circ.ahajournals.org/content/105/8/923.

P. Moreno et al., "Detection of High-Risk Atherosclerotic Coronary Plaques by Intravascular Spectroscopy", J. Interven. Cardiol. 2003; 16:243-252.

J. Wang et al., "Near-Infrared Spectroscopic Characterization of Human Advanced Atherosclerotic Plaques", J. Am. Coll. Cardiol. 2002; 39: 1305-1313.

(56) References Cited

OTHER PUBLICATIONS

A. Nilsson et al., "Near infrared diffuse reflection and laser-induced fluorescence spectroscopy for myocardial tissue characterisation", Spectrochimica Acta Part A: Molecular and Biomolecular Spectroscopy 1997; 53: 1901-1912.
L. Cassis et al., "Near-IR Imaging of Atheromas in Living Arterial Tissue", Anal. Chem. 1993; 65: 1247-1256.
E. Falk, "Multiple culprits in acute coronary syndromes: systemic disease calling for systemic treatment", First published in Ital Heart J, vol. Dec. 1, 2000. (7 pages).

* cited by examiner

ASSESSMENT OF LIPID CORE PLAQUE INTEGRITY

CROSS-REFERENCE TO RELATED APPLICATION

This application claims the benefit of and priority to U.S. Patent Application No. 62/131,140, filed Mar. 10, 2015, and titled "Characterization of Plaque Cap Integrity," the entire contents of which are hereby incorporated by reference.

FIELD OF THE TECHNOLOGY

The present technology relates generally to the field of lipid core plaque cap assessment and detection and, more specifically, to assessing lipid core plaque cap integrity using near-infrared spectroscopy.

BACKGROUND

The location and characteristics of a lipid core plaque (LCP) are important considerations for assessing the risk of the plaque to cause an acute coronary event. LCPs displaying characteristics such as expansive remodeling, increased plaque volume, inflammation, lipid core, and cap thickness below a threshold can be classified as vulnerable LCPs. Vulnerable LCPs are the structures most often implicated, post-mortem, as the culprit lesion in sudden coronary deaths. As a result, the detection of vulnerable LCPs is of great interest to the interventional cardiology community as a tool to assess future risk of LCP rupture. Some existing systems attempt to predict a thickness of the fibrous cap overlying the lipid-filled core. For example, one such system is described in U.S. Pat. No. 8,958,867 to Madden and Raichlen, issued Feb. 17, 2015. However, cap thickness may not provide adequate information about the structure of LCP caps in order to assess their vulnerability to rupture.

SUMMARY OF THE TECHNOLOGY

A need remains for techniques to measure, e.g., the relative presence or depletion of cross-linked collagen in the cap overlying the LCP in order to assess the cap's integrity and likelihood of rupture.

In one aspect, there is a computer-implemented method for building an LCP cap collagen structural integrity classifier. In some embodiments, for each location of a plurality of locations on a plurality of blood vessel walls, the method can include illuminating, with a probe, the location with two or more wavelengths of near-infrared light. The method can include receiving, by the probe, reflected near-infrared light from the location. The method can include determining, by a computing device, a reflectance spectrum based on the reflected near-infrared light from the location. The method can include determining, by the computing device, whether the reflectance spectrum is indicative of a presence of an LCP at the location by applying an LCP classifier to the reflectance spectrum. The method can include selecting, by the computing device, the location if the reflectance spectrum is indicative of the presence of the LCP at the location. The method can include determining, by the computing device, collagen structural integrity indicator data associated with the location. The method can include generating, by the computing device, the LCP cap collagen structural integrity classifier based on the reflectance spectrum and the collagen structural integrity indicator data of each selected location.

In some embodiments, determining, by the computing device, collagen structural integrity indicator data associated with the location includes analyzing, by the computing device, an image of a cross-section of the location, the image being a polarization contrast image of the cross-section stained with Picrosirius red, to determine a measure of cross-linked collagen associated with the location.

In some embodiments, the image is a color image, and determining, by the computing device, collagen structural integrity indicator data associated with the location includes counting, by the computing device, in the image the number of pixels associated with the location that are at least one of red, orange, yellow, and green. In some embodiments, the image is a grayscale image, and determining, by the computing device, collagen structural integrity indicator data associated with the location includes counting, by the computing device, in the image the number of pixels associated with the location that are above a threshold pixel value. In some embodiments, the method can include receiving, by the computing device, a collagen structural integrity threshold, and generating, by the computing device, the LCP cap collagen structural integrity classifier based further on the collagen structural integrity threshold.

In another aspect, there is a computing device including an analysis component. The analysis component can be configured to, for each location of a plurality of locations on a plurality of blood vessel walls: receive a reflectance spectrum, wherein the reflectance spectrum is based on reflected near-infrared light reflected from the location when illuminated with two or more wavelengths of near-infrared light; determine whether the reflectance spectrum is indicative of a presence of a LCP at the location by applying an LCP classifier to the reflectance spectrum; select the location if the reflectance spectrum is indicative of the presence of the LCP at the location; and determine collagen structural integrity indicator data associated with the location. The analysis component can be configured to generate an LCP cap collagen structural integrity classifier based on the reflectance spectrum and the collagen structural integrity indicator data of each selected location.

In some embodiments, the analysis component of the computing device can be further configured to determine collagen structural integrity indicator data associated with the location by analyzing an image of a cross-section of the location, the image being a polarization contrast image of the cross-section stained with Picrosirius red, to determine a measure of cross-linked collagen associated with the location.

In some embodiments, the image is a color image, and the analysis component is further configured to determine collagen structural integrity indicator data associated with the location by counting in the image the number of pixels associated with the location that are at least one of red, orange, yellow, and green. In some embodiments, the image is a grayscale image, and the analysis component is further configured to determine collagen structural integrity indicator data associated with the location by counting in the image the number of pixels associated with the location that are above a threshold pixel value. In some embodiments, the analysis component of the computing device is further configured to receive a collagen structural integrity threshold; and generate the LCP cap collagen structural integrity classifier based on the collagen structural integrity threshold.

Other aspects and advantages of the present technology will become apparent from the following detailed description, taken in conjunction with the accompanying drawings, illustrating the principles of the technology by way of example only.

BRIEF DESCRIPTION OF THE DRAWINGS

The foregoing and other objects, features, and advantages of the present technology, as well as the technology itself, will be more fully understood from the following description of various embodiments, when read together with the accompanying drawings, in which.

DETAILED DESCRIPTION

The technology provides methods and apparatus utilizing near-infrared spectroscopy for the in vivo examination of blood vessel walls and the classification of the integrity of LCP caps. The technology leverages the near-infrared spectral differences between the various biochemical components of LCPs to characterize the relative presence or depletion of cross-linked collagen in the LCP cap in order to assess the LCP cap's integrity.

In some embodiments, the technology can be used to identify plaque characteristics thought to be associated with an LCP's vulnerability to rupture. Such vulnerable LCPs can be generally described as LCPs that are prone, with or without a triggering activity or event of a patient, to events such as ulceration, rupture, or erosion leading to thrombosis causing an acute ischemic syndrome. For example, the technology can be used to non-destructively identify atherosclerotic LCPs with low amounts of cross-linked collagen, which may be vulnerable and more likely to rupture. In some applications, the information about particular LCPs provided by the technology can facilitate physicians in determining the appropriate pharmaceutical or procedural interventions to address those LCPs. In some applications, the information about particular LCPs provided by the technology can facilitate evaluating a particular pharmaceutical's effectiveness for treating LCPs.

Figure 1:
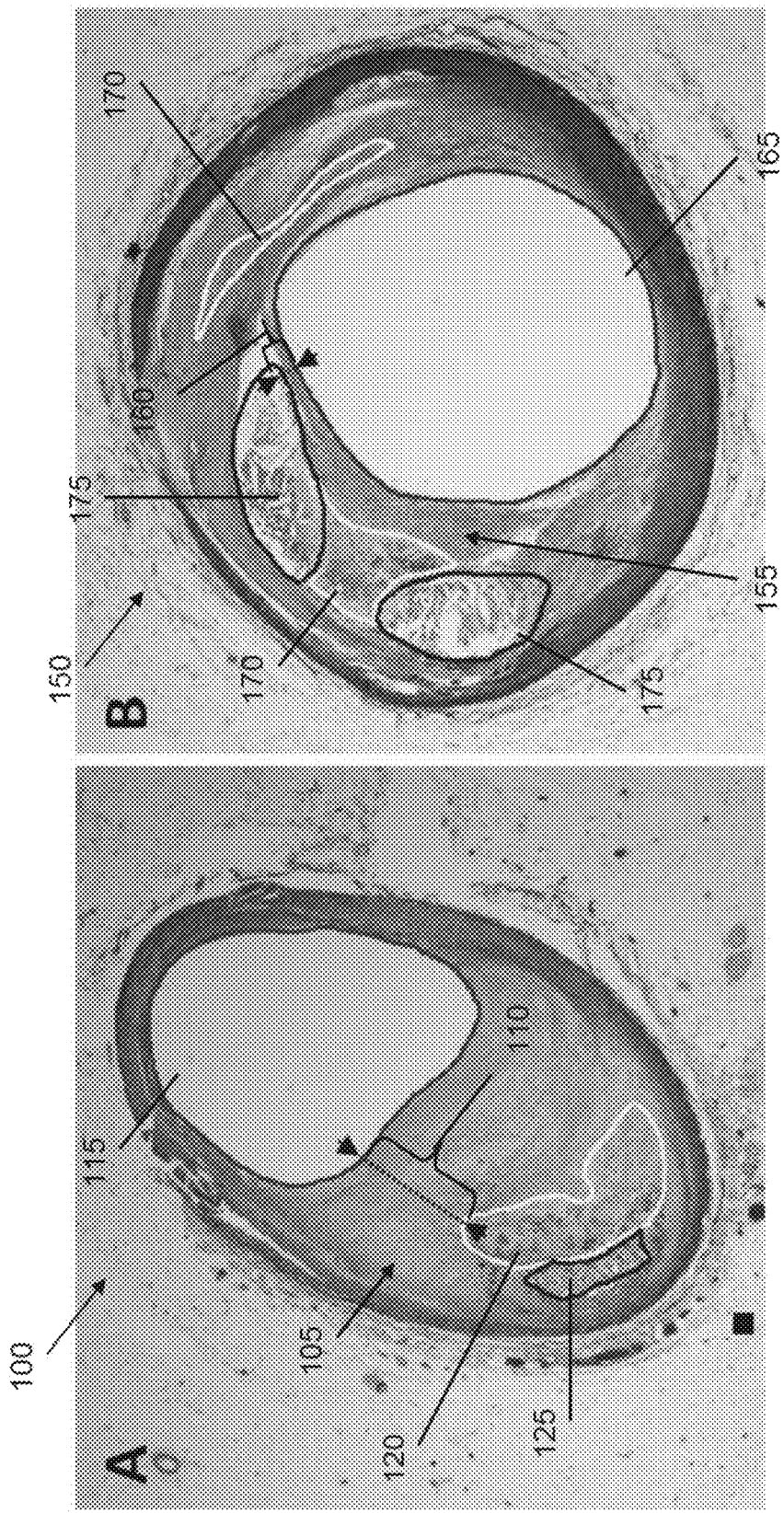
FIG. 1 depicts two sample coronary artery cross sections, each containing LCPs.

FIG. 1 depicts two sample artery cross sections, each containing LCPs. Artery cross section 100 shows the lumen 115, fibrotic tissue 105, and lipid-rich structures consistent with an LCP: lipid pool 120 and necrotic core 125. The fibrotic tissue 105 constitutes a thick cap 110 having high collagen content overlying the lipid-containing portions of the plaque. The high collagen content of the cap can provide greater structural integrity, rendering the cap less vulnerable to rupture. Artery cross section 150 shows lumen 165, fibrotic tissue 155, and lipid-rich structures consistent with an LCP: lipid pools 170 and necrotic cores 175. The fibrotic tissue 155 separating the LCP structures from the lumen 165 has a very thin region 160 with low collagen content. The plaque shown in cross section 150 can be considered vulnerable, as region 160 may be more likely to rupture and release the contents of lipid pools 170 and necrotic cores 175 into lumen 165, which can lead to arterial thrombosis obstructing blood flow to the heart tissue.

Figure 2A:
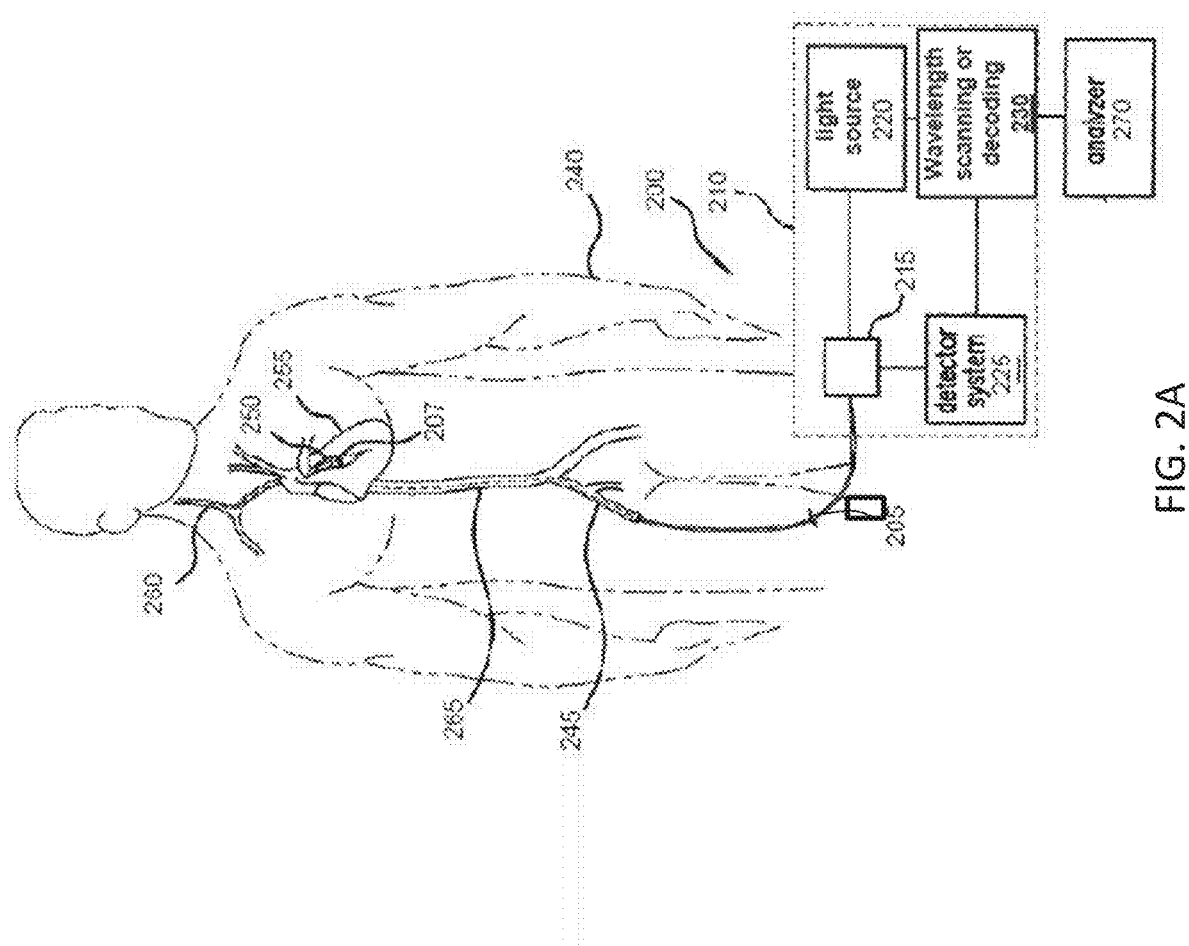
FIG. 2A depicts an optical spectroscopic catheter system.

Various instruments can be used as a part of or in conjunction with the technology to perform near-infrared spectroscopy. FIG. 2A depicts an optical spectroscopic catheter system 200. Catheter system 200 can generally be used for blood vessel analysis. For example, catheter system 200 can be used to illuminate a blood vessel wall with near-infrared light and receive reflected near-infrared light from the blood vessel wall. The technology can use the received reflected near-infrared light to assess the cap integrity and collagen content of detected LCPs. Catheter system 200 includes a probe or catheter 205, and a spectrometer system 210. Catheter 205 can include catheter head 207. Spectrometer system 210 includes pullback and rotation device 215, light source 220, detector system 225, and wavelength scanning or decoding device 230.

Once catheter head 207 is located at a site for examination within a blood vessel, radiation can be generated. In the illustrated example, near-infrared radiation is generated by light source 220 and tuned over a range of wavelengths covering one or more spectral bands of interest. In some embodiments, one or more broadband sources are used to provide the spectral bands of interest, and the signal intensity at various wavelengths is determined using a spectrometer or wavelength encoding methodology. The optical signals can be coupled into the optical fiber of catheter 205 to be transmitted to catheter head 207.

In some embodiments, near-infrared spectral bands are used for spectroscopy. Exemplary spectral bands include light having wavelength of 1000 to 1450 nanometers (nm), 1000 nm to 1350 nm, 1100 nm to 1900 nm, 1150 nm to 1250 nm, 1175 nm to 1280 nm, and 1190 nm to 1250 nm. Other exemplary spectral bands include 1660 nm to 1740 nm, and 1630 nm to 1800 nm. In some implementations, the spectral response is first acquired for a full spectral region and then bands are selected within the full spectral region for further analysis.

In some embodiments, the received, diffusely-reflected, near-infrared light is transmitted back down the optical fibers of catheter 205 to pullback and rotation device 215 or in separate optical fibers. This provides the received radiation or optical signals to a detector system 225, which can comprise one or multiple detectors. Wavelength scanning or decoding device 230 monitors the response of catheter system 200, while controlling light source 220 in order to probe the spectral response of a target area (e.g., an inner wall of a blood vessel) and through the intervening blood or other unwanted signal source, which is typically a fluid. As a result, spectrometer system 210 can collect spectra for multiple locations on the vessel wall. When the acquisitions of the spectra are complete, the spectrometer system 210 can then provide the data to the analyzer 270.

Figure 2B:
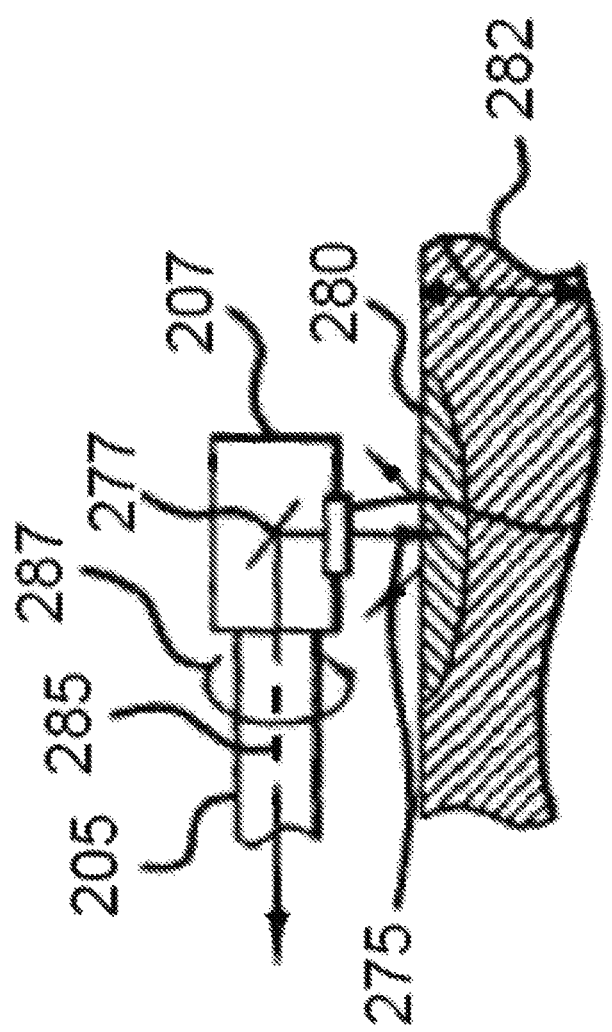
FIG. 2B depicts an alternate view of a portion of the catheter of FIG. 2A.

FIG. 2B depicts an alternate view of a portion of catheter 205 of FIG. 2A. The optical signal 275 (e.g., near-infrared radiation) from the optical fiber of the catheter 205 is directed by fold mirror 277, for example, to exit from the catheter head 207 and impinge on target area 280 of blood vessel wall 282. Catheter head 207 then collects the light that has been diffusely reflected from the target area 280 and the intervening fluid and returns reflected radiation 285 back down catheter 205. In one embodiment, the catheter head 207 spins as illustrated by arrow 287. This allows the catheter head 207 to scan a complete circumference of the blood vessel wall 282. In other embodiments, catheter head 207 includes multiple emitter and detector windows, preferably being distributed around a circumference of the catheter head 207. In some examples, the catheter head 207 is spun while being drawn-back through the length of the portion of the vessel being analyzed.

The analyzer 270 can receive reflected radiation 285 and make an assessment of the blood vessel wall 282 or other tissue of interest (e.g., tissue at area 280 that is opposite catheter head 207). In some embodiments, analyzer 270 determines a reflectance spectrum based on reflected radiation 285. In some embodiments, the reflectance spectrum can be a diffuse reflectance spectrum or log-transformed reflectance spectrum. In some embodiments, an absorbance spectrum can be determined, where absorbance is provided by equation 1.

$$\text{Absorbance} = -\log(I/I_0) \qquad \text{EQN. 1}$$

In equation 1, I is the detected intensity of reflected radiation and $I_0$ is the incident intensity. As will be described in detail below, analyzer 270 can assess the cap integrity and collagen content of LCPs based on the determined spectrum by using a cap collagen structural integrity classifier.

Building an LCP Cap Collagen Structural Integrity Classifier

As noted above, the technology leverages the near-infrared spectral differences between various biochemical components to determine (e.g., predict) the relative presence or depletion of cross-linked collagen overlying the LCP, and, based on this information, assess the cap's integrity. In some embodiments, the technology involves building a mathematical classifier or model to classify the integrity of LCP caps. The mathematical classifier can be developed by modeling the relationship between tissue states of known tissue samples (e.g., samples for which the LCP cap's collagen content is known) and associated spectra for those samples.

Figure 3:
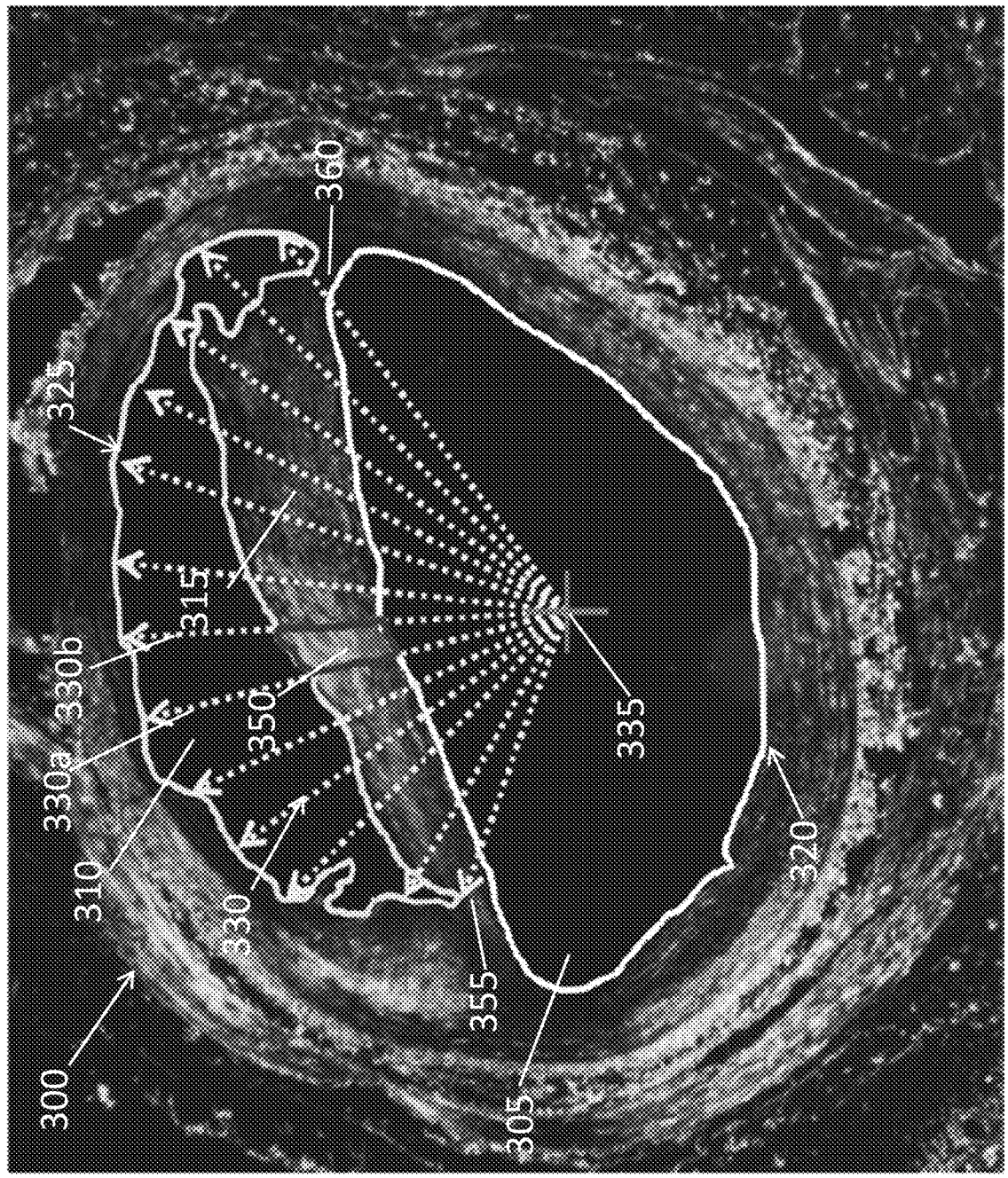
FIG. 3 depicts a Picrosirius (PS) red-stained image of a coronary artery cross section sample.

As a part of building the classifier, locations in blood vessels can be analyzed to measure the presence of collagen in LCP caps. For example, a blood vessel can be sectioned into thin slices to form a series of cross section samples. The samples can then be stained with a collagen-specific Picrosirius (PS) red. PS red staining is a commercially available method for the histological visualization of collagen. For example, the PS red stained blood vessel samples can be prepared by a process of embedding, thin sectioning and PS red staining. The polarization contrast images of the samples can then be taken. Beneficially, the images can highlight the birefringence arising from the cross-linking of the collagen. The polarization contrast images can be used for quantitative morphometric analysis of collagen bundles in LCP caps. Beneficially, in a polarization contrast image of a PS red-stained cross section sample, collagen appears red/orange or green/yellow, while lipid cores appear black. In accordance with the technology, this facilitates the computer-implemented analysis of the collagen presence in the images of the samples. FIG. 3 depicts an image of thin blood vessel cross section sample 300. Cross section sample 300 can be prepared by staining it with PS red and capturing a polarization contrast image, as described above. As illustrated in FIG. 3, cross section 300 includes lumen 305, lipid core 310, and plaque cap 315 (e.g., the region between lumen 305 and lipid core 310). In accordance with the technology, the image of cross section sample 300 can be analyzed to determine the presence of cross-linked collagen in plaque cap 315.

Figure 4:
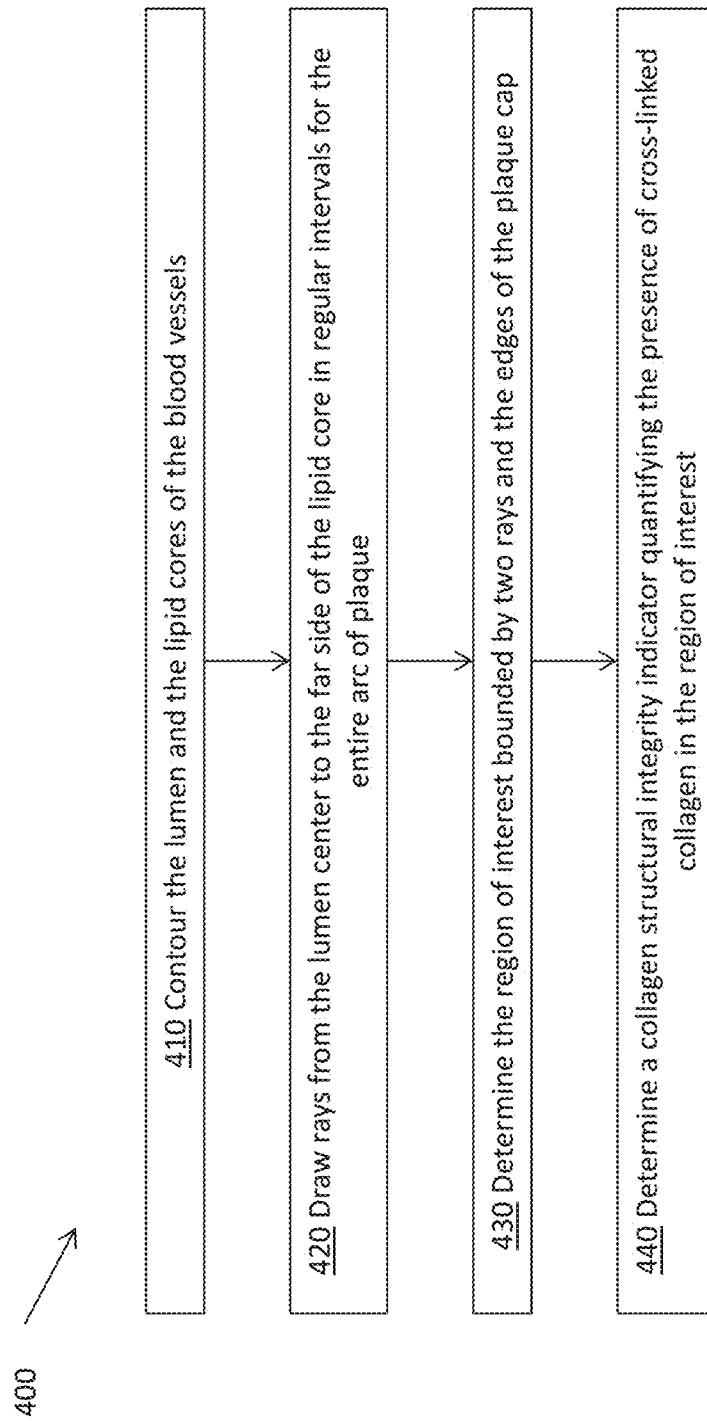
FIG. 4 is a flow chart that depicts a method for analyzing an image of a PS red-stained cross section sample.

FIG. 4 depicts a flow chart 400 for analyzing an image of a PS red-stained cross section sample. The data obtained from the analyzed samples can then be used, along with associated spectra collected from the sample, to build the cap collagen structural integrity classifier. At step 410, the lumen is contoured. For example, the lumen can be contoured by a histologist on an image of a PS red-stained cross section sample. Contouring the lumen can include demarcating the boundary of the lumen. For example, with reference to the image of cross section sample 300, contouring can include drawing boundary line 320 around lumen 305. The lipid core can be contoured in a similar manner. With reference to the image of cross section 300, contouring can include drawing boundary line 325 around lipid core 310. In some embodiments, the boundaries of the lipid core can be determined based on the AHA (American Heart Association) definition, as commonly used by those of skill in the art. At step 420, rays can be drawn from the center of the lumen center to the far side of the lipid core in regular intervals (e.g., 1° intervals) for the entire arc of the plaque. For example, with reference to FIG. 3, rays 330 can be drawn from lumen center 335 in regular intervals for the entire arc of lipid core 310.

At step 430, a region of interest can be determined for a first pair of rays, the region of interest bounded by the two rays and the edges of the plaque cap. For example, with reference to FIG. 3, a region of interest 350 is illustrated as bounded by adjacent rays 330a and 330b and the two contoured edges of plaque cap 315. In some embodiments, adjacent regions of interest can be combined to form a larger region of interest, such as 45° or 90° (a quadrant). For example, larger regions of interest can be used to reduce the uncertainties in angular registration between the collected spectra and the collagen structural integrity indicators determined in step 440. As another example, larger regions of interest can be used to account for limitations in the spatial resolution of the spectroscopy.

At step 440, values for one or more collagen structural integrity indicators can be determined for the region of interest. The structural integrity indicators can be determined by analysis of the polarization contrast image of the PS red-stained cross section sample. High collagen content can correspond to a high measure of pixel colors and/or intensity within the region of interest, and/or low collagen content can correspond to a low measure of pixel colors and intensity within the region of interest. In some embodiments, the collagen structural integrity indicators quantify the presence of cross-linked collagen in the LCP cap in the region of interest. In some embodiments, the collagen structural integrity indicators can be used as a reference for LCP cap integrity. In some embodiments, the collagen structural integrity indicators can be based on measures of pixel colors and/or intensity within the region of interest. For example, the indicator can be calculated by counting the number of red/orange and green/yellow pixels within the region of interest, a higher count indicating a greater presence of collagen in the region of interest. As another example, the indicator can be calculated by summing the grayscale intensity of each pixel in the region of interest. As another example, the number of grayscale pixels above a certain threshold value (e.g., 300-500 for a 16 bit grayscale image) in the region of interest in the image can be summed. In another example, the number of pixels per unit area above a threshold can be measured. In other examples, the maximum or minimum pixel intensity, or complete absence of pixels in the region of interest can be determined. In general, a collagen structural integrity indicator can be any qualitative measure that reflects the degree to which the collagen in the region of interest is present and/or cross-linked. In some embodiments, the values for one or more collagen structural integrity indicators for the region of interest can be determined before regions of interest are combined. In some embodiments, the values for one or more collagen structural integrity indicators for the region of interest can be determined after regions of interest are combined.

Figure 5:
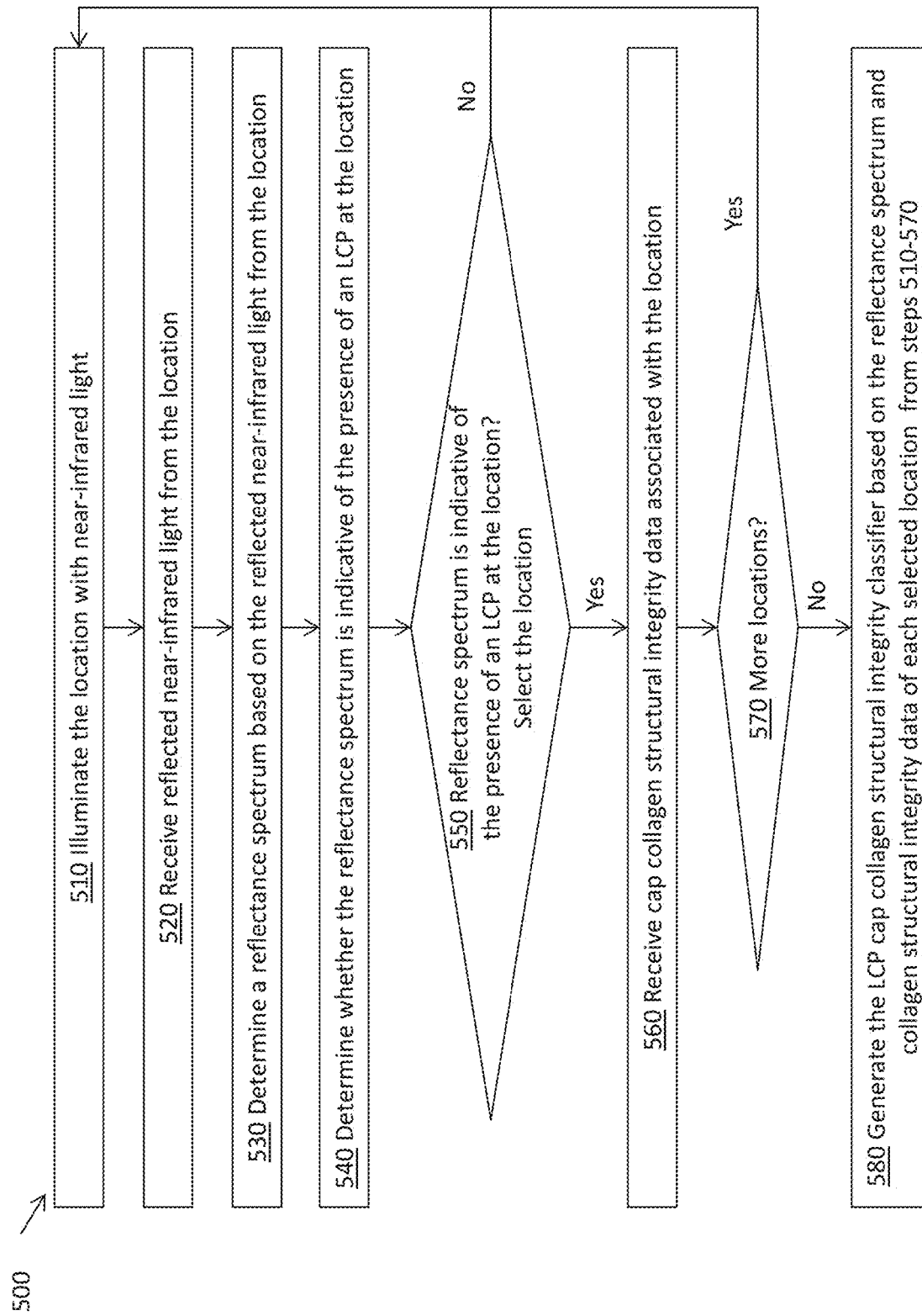
FIG. 5 is a flow chart that depicts a method of building an LCP cap collagen structural integrity classifier.

FIG. 5 is a flow chart 500 that depicts a method of building an LCP cap collagen structural integrity classifier. In some embodiments, spectroscopic catheter system 200 of FIG. 2A can perform the method of building an LCP cap collagen structural integrity classifier. In some embodiments, a separate computing device can perform the method of building an LCP cap collagen structural integrity classifier. At step 510, a location in a blood vessel is illuminated with near-infrared light. As described above with reference to FIG. 2A, catheter system 200, for example, can be used to illuminate a location in a blood vessel with near-infrared light. The near-infrared light can include near-infrared light within a particular spectral band. Exemplary spectral bands include 1000 to 1450 nanometers (nm), 1000 nm to 1350 nm, 1100 nm to 1900 nm, 1150 nm to 1250 nm, 1175 nm to 1280 nm, and 1190 nm to 1250 nm. Other exemplary spectral bands include 1660 nm to 1740 nm, and 1630 nm to 1800 nm. At step 520, reflected near-infrared light from the location is received. For example, catheter system 200 can receive near-infrared light reflected from the location.

At step 530, a reflectance spectrum is determined based on the reflected near-infrared light from the location. In some embodiments, analyzer 270 can determine a reflectance spectrum based on the reflected near-infrared light from the location. In some embodiments, the reflectance spectrum can be a diffuse reflectance spectrum or log-transformed reflectance spectrum. In some embodiments, an absorbance spectrum can be determined.

At step 540, it is determined whether the reflectance spectrum is indicative of the presence of an LCP. In some embodiments, whether the reflectance spectrum is indicative of the presence of an LCP can be determined using the methods described in U.S. Pat. No. 8,000,774, titled "Method and System for Intra Luminal Thrombosis Detection," and filed Jan. 3, 2007 by Sum et al., the entire contents of which are hereby incorporated by reference. In some embodiments, whether the reflectance spectrum is indicative of the presence of an LCP can be determined using the methods described in U.S. Pat. No. 6,816,743, titled "Methods and Apparatus for in vivo Identification and Characterization of Vulnerable Atherosclerotic Plaques," and filed Jan. 24, 2001 by Moreno et al., the entire contents of which are hereby incorporated by reference. At step 550, the location is selected if the reflectance spectrum is indicative of the presence of an LCP at the location.

At step 560, cap integrity data associated with the location is received. The cap integrity data can include the cap collagen structural integrity indicators determined for the location as described in connection with FIG. 4. At step 570, it is determined whether there are more vessel wall locations from which to collect data. If there are more locations in the plurality of vessels left from which to receive spectra and histopathology data, steps 510-560 are repeated for each remaining location. Otherwise, the method proceeds to step 580.

At step 580, the LCP cap collagen structural integrity classifier is generated based on the reflectance spectrum and histopathology data of each selected location from steps 510-570. In some embodiments, the data is set up as an "x-block" matrix, where each row represents a spectrum for a corresponding location, and a "y-block" vector of cap collagen structural integrity data (e.g., collagen structural integrity indicator values) for the corresponding location. In some embodiments, a collagen structural integrity threshold is applied to the vector of cap collagen structural integrity data. In some embodiments, the cap integrity threshold is applied to the vector of cap collagen structural integrity data, resulting in a "y-block" that indicates the presence or absence of a cap with collagen content less than the cap integrity threshold. Application of the collagen structural integrity threshold can include placing the values of the cap collagen structural integrity data into classes. For example, the values of the cap collagen can be separated into classes of "high cross-linked collagen content" and "low cross-linked collagen content" based on the threshold. The resulting "y-block" would then include an indication for each spectrum whether it is indicative of "high cross-linked collagen content" or "low cross-linked collagen content." In some embodiments, more than one collagen structural integrity threshold can be used to place the data into more than two classes.

The cap collagen structural integrity classifier can then be generated using any of several multivariate techniques, such as multivariate mathematical models developed by modeling the relationship between the reflectance spectra and histopathology data for each location. The mathematical models can be based upon techniques such as Partial Least Squares Discrimination Analysis (PLS-DA), Principle Component Analysis with Mahalanobis Distance and augmented Residuals (PCA/MDR), and others such as PCA with K-nearest neighbor, PCA with Euclidean Distance, SIMCA, the bootstrap error-adjusted single-sample technique (BEST), neural networks and support vector machines, and other types of discrimination means.

In some embodiments, the cap collagen structural integrity classifier can be generated without determining whether the reflectance spectrum is indicative of the presence of an LCP at the location (e.g., step 540). If the reflectance spectrum is associated with a location without an LCP (e.g., as determined by histological analysis of the sample associated with that location), a predetermined value can be used for the associated cap collagen structural integrity indicators. For example, the value for a cap collagen structural integrity indicator can be automatically set to a value indicating a high presence of collagen.

Examining a Blood Vessel Wall

Figure 6:
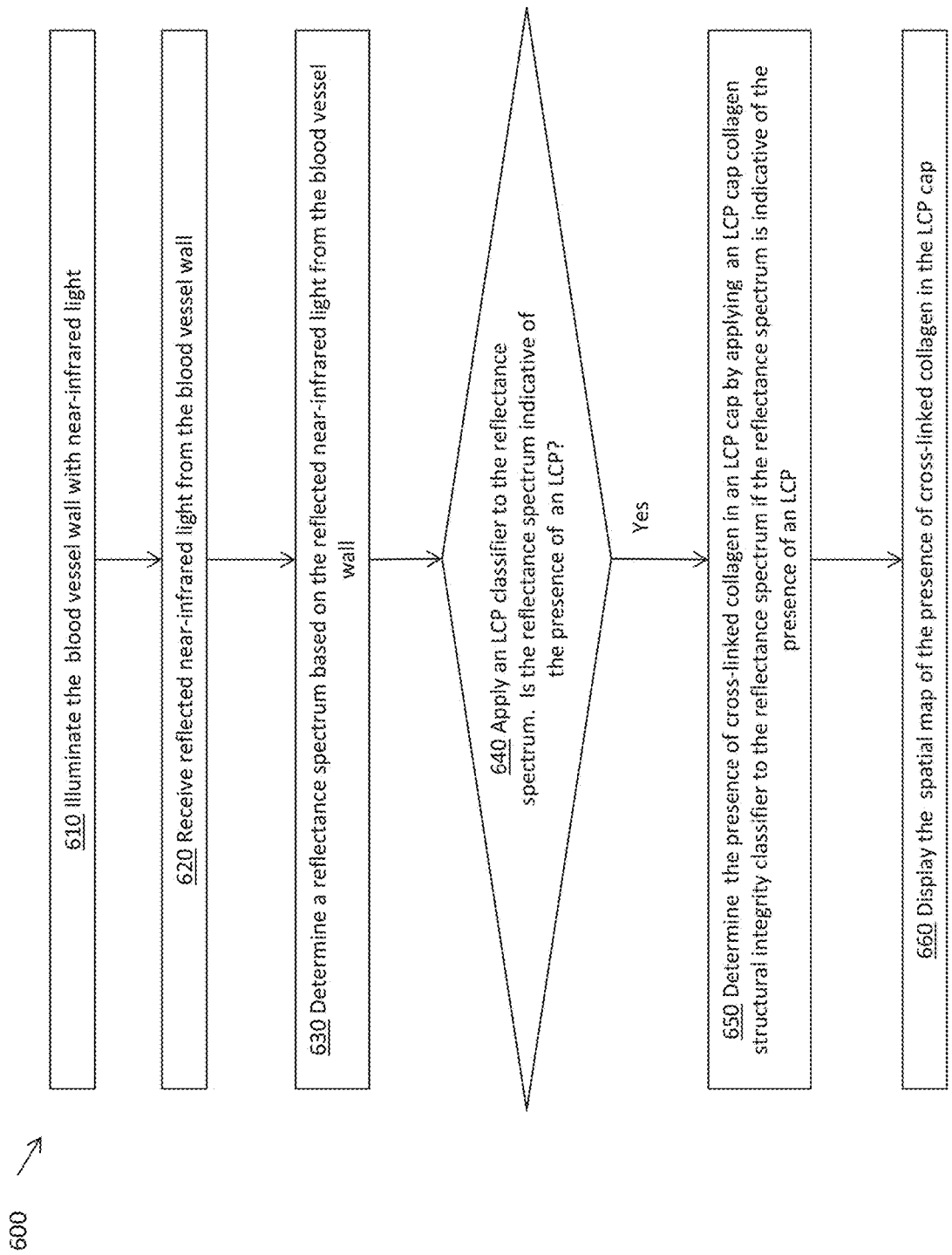
FIG. 6 is a flow chart that depicts a method for examining a blood vessel wall and generating the spatial map of the collagen content of the LCP caps.

In some embodiments, the technology involves a method of examining a blood vessel wall and generating the spatial map of the content of collagen in the LCP caps. FIG. 6 is a flow chart 600 that depicts a method for examining a blood vessel wall. In some embodiments, spectroscopic catheter system 200 of FIG. 2A can perform the method of examining a blood vessel wall. In some embodiments, a separate computing device can perform the method of examining a blood vessel wall.

At step 610, the blood vessel wall is illuminated with near-infrared light. As described above with reference to FIG. 2A, catheter system 200, for example, can be used to illuminate a blood vessel wall with near-infrared light. The near-infrared light can include near-infrared light within a particular spectral band. Exemplary spectral bands include 1000 to 1450 nanometers (nm), 1000 nm to 1350 nm, 1100 nm to 1900 nm, 1150 nm to 1250 nm, 1175 nm to 1280 nm, and 1190 nm to 1250 nm. Other exemplary spectral bands include 1660 nm to 1740 nm, and 1630 nm to 1800 nm. At step 620, reflected near-infrared light from the blood vessel wall is received. For example, catheter system 200 can receive near-infrared light reflected from the location.

At step 630, a reflectance spectrum is determined based on the reflected near-infrared light from the blood vessel wall. In some embodiments, analyzer 270 can determine a reflectance spectrum based on the reflected near-infrared light from the blood vessel wall. In some embodiments, the reflectance spectrum can be a diffuse reflectance spectrum or log-transformed diffuse reflectance spectrum. In some embodiments, an absorbance spectrum can be determined.

At step 640, it is determined whether the reflectance spectrum is indicative of the presence of an LCP. Any of the techniques previously described with respect to step 550 of FIG. 5 can be used. If the reflectance spectrum is indicative of the presence of an LCP, the method proceeds to step 650.

At step 650, the presence of cross-linked collagen in an LCP cap is determined by applying an LCP cap collagen structural integrity classifier to the reflectance spectrum if the reflectance spectrum is indicative of the presence of an LCP. In some embodiments, the LCP cap collagen structural integrity classifier can be a classifier generated as described above with reference to FIG. 4. The LCP cap collagen structural integrity classifier can be applied to the spectrum to characterize the tissue at a particular location along the vessel wall. For example, application of the LCP cap collagen structural integrity classifier to the reflectance spectrum can provide a probability that the spectrum is indicative of an LCP cap with collagen content greater than the cap integrity threshold used to build the LCP cap collagen structural integrity classifier. The presence of cross-linked collagen can be determined to be greater than the cap integrity threshold if the probability provided by the classifier exceeds a threshold (e.g., 0.6). Application of the LCP cap collagen structural integrity classifier to the reflectance spectrum can provide a probability that the spectrum is indicative of an LCP cap with presence of cross-linked collagen less than the cap integrity threshold used to build the LCP cap collagen structural integrity classifier. In such embodiments, the presence of cross-linked collagen in the cap is determined to be less than the cap integrity threshold if the probability provided by the classifier exceeds a threshold (e.g., 0.6). In another example, application of the LCP cap collagen structural integrity classifier to the reflectance spectrum can provide a predicted value for the cap collagen structural integrity indicator for the relevant portion of the LCP cap, such as when a cap integrity threshold is not used to build the LCP cap collagen structural integrity classifier.

In some embodiments, multiple classifiers can be applied. For example, a first classifier can be applied with a cap integrity threshold corresponding to a high collagen content LCP cap and a second classifier can be applied using a cap integrity threshold corresponding to a low collagen content LCP cap.

Figure 7:
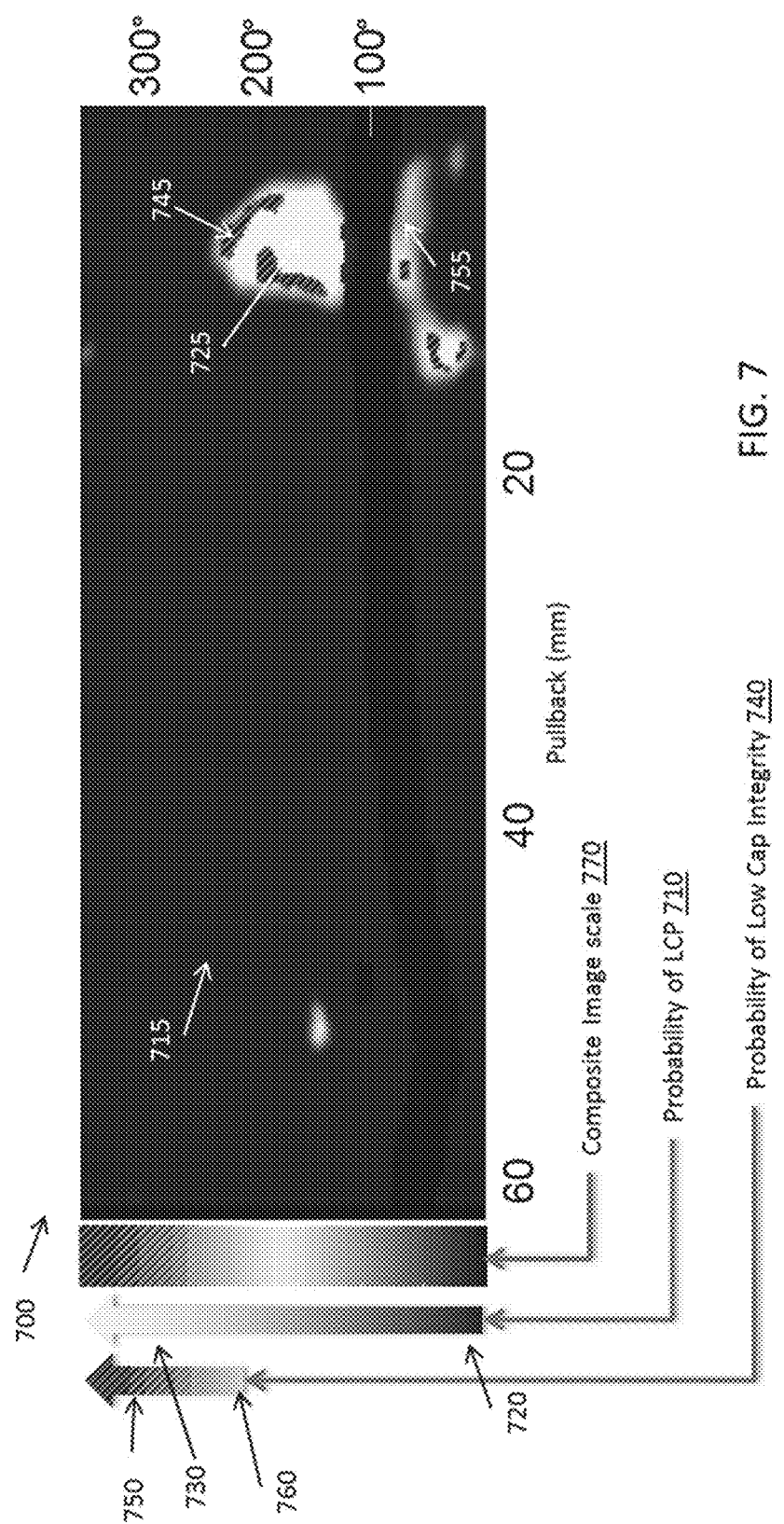
FIG. 7 depicts an exemplary graphical display for displaying the spatial maps of the collagen content of LCP caps.

At step 660, the spatial map of the presence of cross-linked collagen in the LCP cap is displayed. In some embodiments, the spatial maps of the collagen content of the LCP cap are displayed on a graphical display. FIG. 7 depicts an exemplary graphical display 700 for displaying the spatial maps of the collagen content of LCP caps. In the spatial map, the x-axis scale represents pullback (e.g., the distance which is normal to the radius of the lumen) in millimeters (mm), and the y-axis represents the position in degrees (°) around the circumference of the lumen which spans 360°. The graphical display 700 shows a spatially-resolved view of the presence of LCPs, as provided by an LCP classifier, for example. As described above, application of an LCP cap collagen structural integrity classifier to the reflectance spectrum can provide a probability that the spectrum is indicative of an LCP cap with the presence of cross-linked collagen greater than the cap integrity threshold used to build the LCP cap collagen structural integrity classifier. The shading scale 710 maps the probability of the presence of LCP to a two-shade scale. The heavily-shaded regions indicate locations in the vessel with a low probability of LCP, for example, location 715 and its corresponding scale location 720 on the shading scale 710. The lightly-shaded regions indicate locations in the vessel with a high probability of LCP, for example, location 725 and its corresponding scale location 730 on the shading scale 710. Within the identified LCPs, the shading scale 740 represents the probability of cap integrity in a two-shade scale. Heavily shaded regions within the LCP, for example, location 745 and its corresponding scale location 750 on the shading scale 740, indicate locations in the vessel with low probability of high cap integrity, as predicted by application of the LCP cap collagen structural integrity classifier. Lightly shaded regions within the LCP, for example, location 755 and its corresponding scale location 760 on the shading scale 740, indicate locations in the vessel with high probability of high cap integrity, as predicted by application of the LCP cap collagen structural integrity classifier. In the illustrated embodiment, the two shading scales 710 and 740 can be combined or overlaid to have the composite image scale 770 to indicate the probability of LCP and the probability of cap collagen structural integrity.

In some embodiments, the method for examining a blood vessel wall can be executed without determining whether the reflectance spectrum is indicative of the presence of an LCP at the location (e.g., step 640). In some embodiments, the cap collagen structural integrity classifier can be applied to all of the received reflectance spectra.

The above-described techniques can be implemented in digital electronic circuitry, or in computer hardware, firmware, software, or in combinations of them. The implementation can be as a computer program product, i.e., a computer program tangibly embodied in an information carrier, e.g., in a machine-readable storage device, for execution by, or to control the operation of, a data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a communication network.

Method steps can be performed by one or more programmable processors executing a computer program to perform functions of the invention by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. Generally, a computer also includes, or can be operatively coupled to receive data from or transfer data to, or both, one or more mass storage devices for storing data, e.g., magnetic, magneto-optical, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the above described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks.

The computing system can include clients and servers. A client and server are generally remote from each other and typically interact through a communication network. The relationship of client and server arises by virtue of computer programs running on the respective computers and having a client-server relationship to each other.

The technology has been described in terms of particular embodiments. The alternatives described herein are examples for illustration only and not to limit the alternatives in any way. The steps of the described methods can be performed in a different order and still achieve desirable results. Other embodiments are within the scope of the following claims.

What is claimed is:

1. A computer-implemented method for building a lipid core plaque (LCP) cap collagen structural integrity classifier comprising:
   a. for each location of a plurality of locations on a plurality of blood vessel walls:
      illuminating, with a probe, the location with two or more wavelengths of near-infrared light;
      receiving, by the probe, reflected near-infrared light from the location;
      determining, by a computing device, a reflectance spectrum based on the reflected near-infrared light from the location;
      determining, by the computing device, whether the reflectance spectrum is indicative of a presence of an LCP at the location by applying an LCP classifier to the reflectance spectrum;
      selecting, by the computing device, the location if the reflectance spectrum is indicative of the presence of the LCP at the location; and
      determining, by the computing device, collagen structural integrity indicator data associated with the location; and
   b. generating, by the computing device, the LCP cap collagen structural integrity classifier based on the reflectance spectrum and the collagen structural integrity indicator data of each selected location from step a, the LCP cap collagen structural integrity classifier including an x-block matrix, wherein each row in the x-block matrix represents a spectrum for a corresponding location on the plurality of blood vessel walls, and a y-block vector of cap collagen structural integrity data for the corresponding location.

2. The method of claim 1, wherein determining, by the computing device, collagen structural integrity indicator data associated with the location comprises:
   a. analyzing, by the computing device, an image of a cross-section of the location, the image being a polarization contrast image of the cross-section stained with Picrosirius red, to determine a measure of cross-linked collagen associated with the location.

3. The method of claim 2, wherein the image is a color image, and wherein determining, by the computing device, collagen structural integrity indicator data associated with the location comprises:
   a. counting, by the computing device, in the image the number of pixels associated with the location that are at least one of red, orange, yellow, and green.

4. The method of claim 2, wherein the image is a grayscale image, and wherein determining, by the computing device, collagen structural integrity indicator data associated with the location comprises:
   a. counting, by the computing device, in the image the number of pixels associated with the location that are above a threshold pixel value.

5. The method of claim 1, further comprising:
   a. receiving, by the computing device, a collagen structural integrity threshold; and
   b. generating, by the computing device, the LCP cap collagen structural integrity classifier based further on the collagen structural integrity threshold.

6. A computing device comprising:
   a. an analysis component configured to:
      i. for each location of a plurality of locations on a plurality of blood vessel walls:
         receive a reflectance spectrum, wherein the reflectance spectrum is based on reflected near-infrared light reflected from the location when illuminated with two or more wavelengths of near-infrared light;
         determine whether the reflectance spectrum is indicative of a presence of a lipid core plaque (LCP) at the location by applying an LCP classifier to the reflectance spectrum;
         select the location if the reflectance spectrum is indicative of the presence of the LCP at the location; and
         determine collagen structural integrity indicator data associated with the location; and ii. generate an LCP cap collagen structural integrity classifier based on the reflectance spectrum and the collagen structural integrity indicator data of each selected location from step i, the LCP cap collagen structural integrity classifier including an x-block matrix, wherein each row in the x-block matrix represents a spectrum for a corresponding location on the plurality of blood vessel walls, and a y-block vector of cap collagen structural integrity data for the corresponding location.

7. The computing device of claim 6, wherein the analysis component is further configured to determine collagen structural integrity indicator data associated with the location by:
   a. analyzing an image of a cross-section of the location, the image being a polarization contrast image of the cross-section stained with Picrosirius red, to determine a measure of cross-linked collagen associated with the location.

8. The computing device of claim 7, wherein the image is a color image, and wherein the analysis component is further configured to determine collagen structural integrity indicator data associated with the location by:
   a. counting in the image the number of pixels associated with the location that are at least one of red, orange, yellow, and green.

9. The computing device of claim 7, wherein the image is a grayscale image, and wherein the analysis component is further configured to determine collagen structural integrity indicator data associated with the location by:
   a. counting in the image the number of pixels associated with the location that are above a threshold pixel value.

10. The computing device of claim 6, wherein the analysis component is further configured to:
   a. receive a collagen structural integrity threshold; and
   b. generate the LCP cap collagen structural integrity classifier based on the collagen structural integrity threshold.

* * * * *